(12) United States Patent
Stierli et al.

(10) Patent No.: US 8,552,049 B2
(45) Date of Patent: Oct. 8, 2013

(54) PYRAZOLECARBOXAMIDE DERIVATIVES AND THEIR USE AS MICROBIOCIDES

(75) Inventors: Daniel Stierli, Stein (CH); Harald Walter, Stein (CH)

(73) Assignee: Syngenta Corp Protection, LLC, Greensboro, NC (US)

( * ) Notice: Subject to any disclaimer, the term of this patent is extended or adjusted under 35 U.S.C. 154(b) by 0 days.

(21) Appl. No.: 13/700,706

(22) PCT Filed: May 12, 2011

(86) PCT No.: PCT/EP2011/057682
§ 371 (c)(1),
(2), (4) Date: Nov. 28, 2012

(87) PCT Pub. No.: WO2011/147690
PCT Pub. Date: Dec. 1, 2011

(65) Prior Publication Data
US 2013/0072535 A1 Mar. 21, 2013

(30) Foreign Application Priority Data
May 28, 2010 (EP) .................................. 10164293

(51) Int. Cl.
*A61K 31/415* (2006.01)
*C07D 231/10* (2006.01)
*C07C 239/00* (2006.01)

(52) U.S. Cl.
USPC .......... 514/406; 548/374.1; 564/300

(58) Field of Classification Search
USPC .......... 514/406; 548/374.1; 564/300
See application file for complete search history.

(56) References Cited

FOREIGN PATENT DOCUMENTS

EP 1792901 6/2007

OTHER PUBLICATIONS

International Search Report, International Application No. PCT/EP2011/057682, completion date: Jun. 24, 2011.
Chemical Abstracts Service, Columbus, Ohio, US; retrieved from STN accession No. 1984: 490922, abstract; RN 91486-48-5, 91486-49-6, 91486-50-9.

*Primary Examiner* — Samantha Shterengarts
(74) *Attorney, Agent, or Firm* — R. Kody Jones

(57) ABSTRACT

Compounds of Formula (I) wherein $R_1$ is $C_1$-$C_4$alkyl or $C_1$-$C_4$haloalkyl; $R_2$ is $C_1$-$C_4$alkyl; $R_3$ is hydrogen or halogen; $R_4$ is hydrogen, $C_1$-$C_4$alkyl or $C_1$-$C_4$halogenalkyl; $R_5$ is hydrogen, halogen, $C_1$-$C_4$alkyl or $C_1$-$C_4$halogenalkyl; $R_6$ is hydrogen, halogen, $C_1$-$C_4$alkyl, $C_2$-$C_6$alkenyl or $C_3$-$C_6$alkinyl; $R_7$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl, $C_1$-$C_6$haloalkyl, $C_1$-$C_6$haloakoxy, $C_2$-$C_6$haloalkenyl, or $C_2$-$C_6$haloalkenyloxy; $R_8$ is hydrogen, halogen, $C_1$-$C_4$alkyl, $C_2$-$C_6$alkenyl or $C_3$-$C_6$alkinyl; with the provisio that at least one of $R_6$, $R_7$ and $R_8$ is different from hydrogen; n is 0 or 1, are suitable for use as microbriocides.

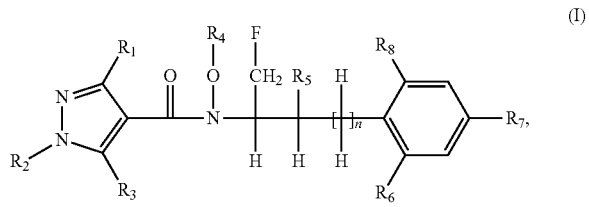

(I)

11 Claims, No Drawings

PYRAZOLECARBOXAMIDE DERIVATIVES AND THEIR USE AS MICROBIOCIDES

This application is a 371 of International Application No. PCT/EP2011/057682 filed May 12, 2011, which claims priority to EP 10164293.2 filed May 28, 2010, the contents of which are incorporated herein by reference.

The present invention relates to novel microbiocidally active, in particular fungicidally active, carboxamides. It further relates to intermediates used in the preparation of these compounds, to compositions which comprise these compounds and to their use in agriculture or horticulture for controlling or preventing infestation of plants by phytopathogenic microorganisms, preferably fungi.

Fungicidally active carboxamides are described, for example, in EP 1787981A1 and EP 1792901A1. It has been found that novel carboxamides with a specific substitution pattern have microbiocidal activity.

The present invention accordingly relates to N-alkoxycarboxamides of formula I

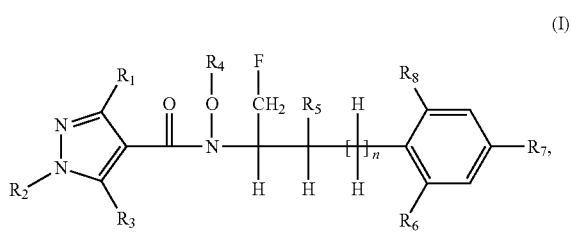

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$halogenalkyl;
$R_5$ is hydrogen, halogen, $C_1$-$C_4$alkyl or $C_1$-$C_4$halogenalkyl;
$R_6$ is hydrogen, halogen, $C_1$-$C_4$alkyl, $C_2$-$C_6$alkenyl or $C_3$-$C_6$alkinyl;
$R_7$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl, $C_1$-$C_6$haloalkyl, $C_1$-$C_6$haloalkoxy, $C_2$-$C_6$haloalkenyl, or $C_2$-$C_6$haloalkenyloxy;
$R_8$ is hydrogen, halogen, $C_1$-$C_4$alkyl, $C_2$-$C_6$alkenyl or $C_3$-$C_6$alkinyl; with the proviso that at least one of $R_6$, $R_7$ and $R_8$ is different from hydrogen;
n is 0 or 1; and agronomically acceptable salts/isomers/structural isomers/stereoisomers/diastereoisomers/enantiomers/tautomers and N-oxides of those compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, alkenyl and alkynyl radicals are derived from the alkyl radicals mentioned. The alkenyl and alkynyl groups can be mono- or di-unsaturated. The cycloalkyl groups occurring in the definitions of the substituents are, for example, cyclopropyl, cyclobutyl, cyclopentyl or cyclohexyl. Halogen is generally fluorine, chlorine, bromine or iodine, preferably fluorine, bromine or chlorine. This also applies, correspondingly, to halogen in combination with other meanings, such as halogenalkyl or halogenalkoxy. Haloalkyl groups preferably have a chain length of from 1 to 4 carbon atoms. Halonalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

In preferred compounds of formula I, independently from each other,
a) $R_1$ is difluoromethyl, trifluoromethyl or methyl,
b) $R_2$ is methyl;
c) $R_3$ is hydrogen or fluoro;
d) $R_4$ is hydrogen, methyl or ethyl;
e) $R_4$ is methyl;
f) $R_5$ is hydrogen or methyl;
g) n is 0;
h) $R_6$, $R_7$ and $R_8$ are, independently from each other, hydrogen or chloro; with the proviso that at least one of $R_6$, $R_7$ and $R_8$ is different from hydrogen;
j) $R_7$ is chloro, bromo or $C_1$-$C_4$alkyl.

Especially preferred compounds of formula I are those, wherein
$R_1$ is difluoromethyl or trifluoromethyl;
$R_2$ is methyl;
$R_3$ is hydrogen;
$R_4$ is methyl;
$R_6$, $R_7$ and $R_8$ are, independently from each other, hydrogen or halogen, preferably hydrogen or chloro; with the proviso that at least one of $R_6$, $R_7$ and $R_8$ is different from hydrogen.

Further compounds of formula I are preferred, wherein $R_5$ is hydrogen.

In an especially preferred group of compounds of formula I,
$R_1$ is difluoromethyl, trifluoromethyl or methyl,
$R_2$ is methyl;
$R_3$ is hydrogen or fluoro;
$R_4$ is methyl;
$R_5$ is hydrogen or methyl; preferably hydrogen;
n is 0;
$R_6$, $R_7$ and $R_8$ are, independently from each other, hydrogen or chloro; with the proviso that at least one of $R_6$, $R_7$ and $R_8$ is different from hydrogen;

In another especially preferred group of compounds of formula I,
$R_1$ is $C_1$-$C_4$haloalkyl, especially difluoromethyl;
$R_2$ is $C_1$-$C_4$alkyl, especially methyl;
$R_3$ is hydrogen;
$R_4$ is $C_1$-$C_4$alkyl, especially methyl;
$R_5$ is hydrogen;
n is 0 or 1;
$R_6$ is hydrogen or halogen, especially hydrogen or chloro;
$R_7$ is halogen, especially chloro; and $R_8$ is hydrogen or halogen, especially hydrogen or chloro; with the proviso that at least one of $R_6$, $R_7$ and $R_8$ is different from hydrogen. In this group of especially preferred compounds, n is 0.

Further compounds of formula I are preferred, wherein $R_6$ and $R_7$ are chloro.

Further compounds of formula I are preferred, wherein $R_6$, $R_7$ and $R_8$ are chloro.

Especially preferred compounds of formula I are selected from the group consisting of 3-Difluoromethyl-1-methyl-1H-pyrazole-4-carboxylic acid [2-(2,4-chloro-phenyl)-1-fluoromethyl-ethyl]-methoxy-amide;

3-difluoromethyl-1-methyl-1H-pyrazole-4-carboxylic acid [1-fluoromethyl-2-(2,4,6-trichlorophenyl)-ethyl]-methoxy-amide;

1-methyl-3-trifluoromethyl-1H-pyrazole-4-carboxylic acid [1-fluoromethyl-2-(2,4,6-trichlorophenyl)-ethyl]-methoxy-amide;

5-fluoro-1,3-dimethyl-1H-pyrazole-4-carboxylic acid [1-fluoromethyl-2-(2,4,6-trichlorophenyl)-ethyl]-methoxy-amide; and 3-difluoromethyl-1-methyl-1H-pyrazole-4-carboxylic acid [3-(4-chloro-phenyl)-1-fluoromethyl-propyl]-methoxy-amide.

Compounds of formula I may be prepared by reacting a compound of formula II

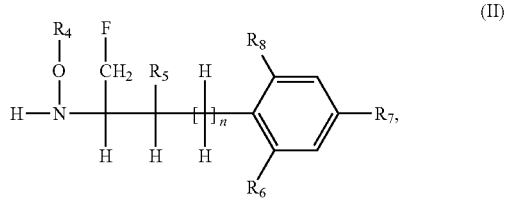

wherein $R_4$, $R_5$, n, $R_6$, $R_7$ and $R_8$ are as defined under formula I; with a compound of formula III

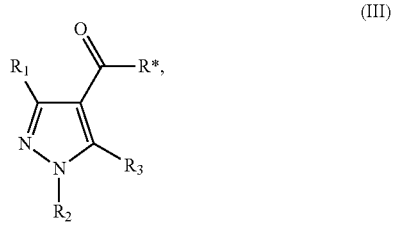

in which $R_1$, $R_2$ and $R_3$ are as defined under formula I, and $R^*$ is halogen, hydroxy or $C_{1-6}$ alkoxy, preferably chloro. Compounds of formula III are known and described, for example in U.S. Pat. No. 5,093,347 and WO 2008/148570 or can be prepared by methods known in the art. For example, the compound of formula IIIa

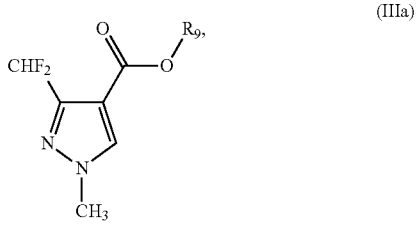

wherein $R_9$ is $C_1$-$C_6$alkyl, can be prepared by reacting a compound of formula IIIb

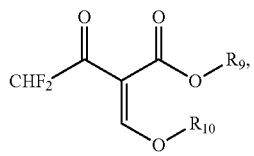

wherein $R_9$ is as defined for formula IIIa and $R_{10}$ is $C_1$-$C_6$alkyl, with methylhydrazine in the presence of water, a hydroxide base and an organic solvent selected from an aromatic hydrocarbon and a halogen-substituted aromatic hydrocarbon.

The reactions to give compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

When $R^*$ is hydroxy, a coupling agent, such as benzotriazol-1-yloxytris(dimethylamino)phosphoniumhexafluorophosphate, bis-(2-oxo-3-oxazolidinyl)-phosphinic acid chloride (BOP—Cl), N,N'-dicyclohexylcarbodiimide (DCC) or 1,1'-carbonyl-diimidazole (CDI), may be used.

The Intermediates of the Formula II

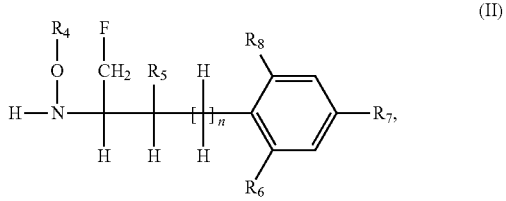

wherein $R_4$, $R_5$, n, $R_6$, $R_7$ and $R_8$ are as defined under formula I, preferably wherein $R_4$ is $C_1$-$C_4$alkyl; are novel and were developed specifically for the preparation of the compounds of formula I. Accordingly, these intermediates of the formula II also form a part of the subject-matter of the present invention.

The preferred substituent definitions for the compounds of formula I are also valid for the compound of formula II. Thus, for example, preferred compounds of formula II are those, wherein, independently from each other, a) $R_4$ is hydrogen, methyl or ethyl;
b) $R_4$ is methyl;
c) $R_5$ is hydrogen or methyl;
d) n is 0;
e) $R_6$, $R_7$ and $R_8$ are hydrogen or chloro; with the proviso that at least one of $R_6$, $R_7$ and $R_8$ is different from hydrogen;
f) $R_7$ is chloro, bromo or $C_1$-$C_4$alkyl.

Intermediates of Formula IIA

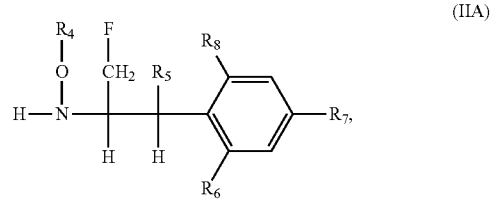

wherein $R_4$, $R_5$, $R_6$, $R_7$ and $R_8$ are as defined under formula I may be prepared as described in reaction scheme 1.

Scheme 1:

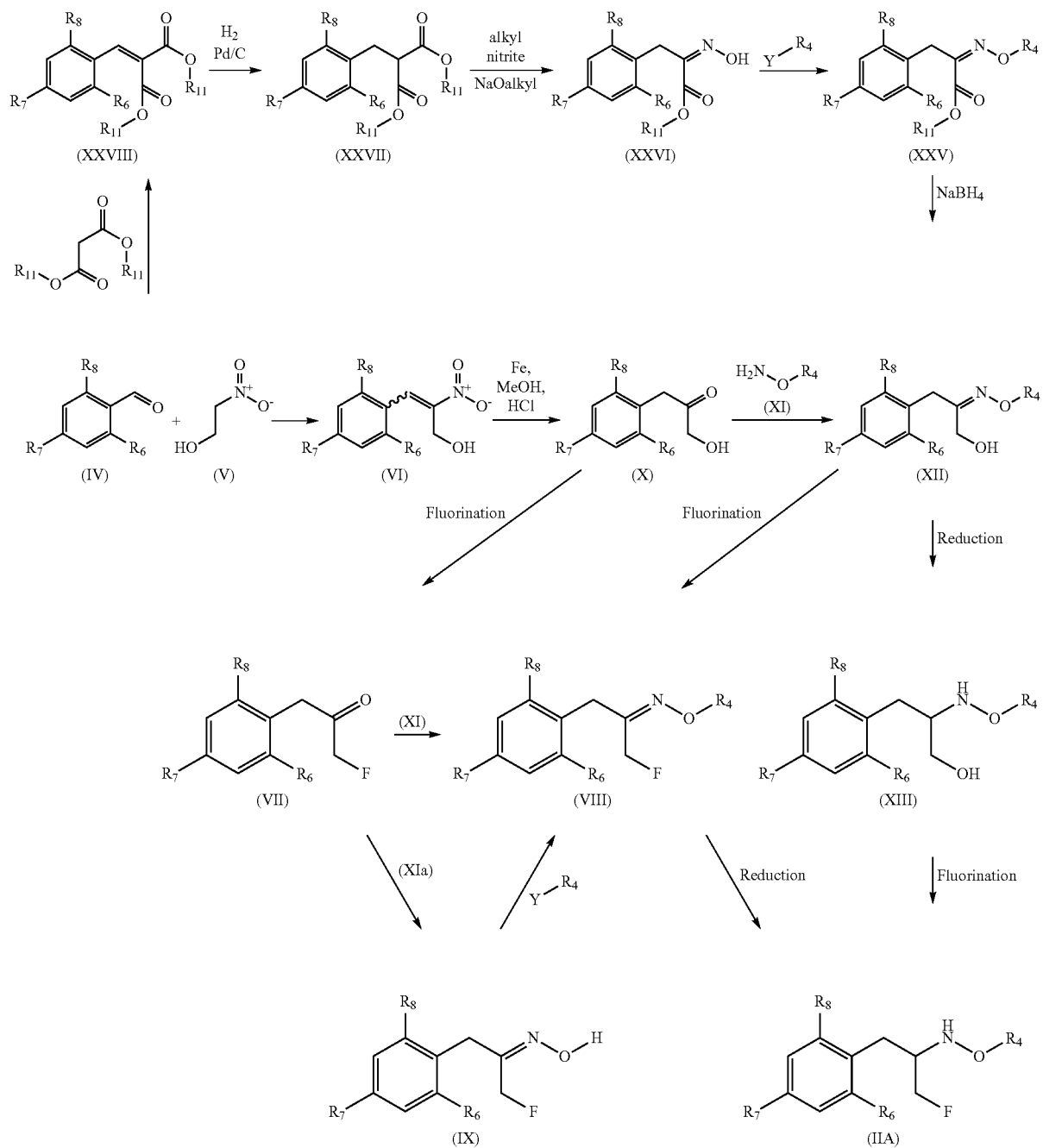

3-Aryl-2-nitroprop-en-1-ol of formula VI, in which $R_6$, $R_7$ and $R_8$ are as defined under formula IIA, can be prepared by a Henry-reaction (nitroaldol-reaction) of 2-nitroethanol of formula V, with a carbonyl compound of formula (IV), in which $R_6$, $R_7$ and $R_8$ are as defined under formula IIA, in the presence of acetic acid and ammonium acetate at temperatures between ambient temperature and reflux temperature. (J. Org. Chem. 2008, Vol. 73, No. 10, 3745-3753)

3-Aryl-2-nitroprop-en-1-ol of formula VI, in which $R_6$, $R_7$ and $R_8$ are as defined under formula IIA, may be reduced with iron and hydrochloric acid to give oximes that will be further hydrolyzed to hydroxyphenylpropanones of formula X, in which $R_6$, $R_7$ and $R_8$ are as defined under formula IIA, as it is described, for example, in M. Kulka and H. Hibbert *J. Am. Chem. Soc.* 65, 1180 (1943) and in Prasun K. Pradhan et al. *Synthetic Commun.*, 35, 913-922, 2005. The reaction is carried out at temperatures of between 40-100° C. in a convenient organic solvent such as methanol, ethanol, tert-butanol, trifluoroethanol or dioxane.

O-alkoxy oxime derivatives of formula XII and VIII may be prepared by oximation of phenylpropanones of formula X and VII with O-alkyl hydroxylamine derivatives of formula XI or a salt thereof.

Suitable solvents carrying out the oximation step are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide, N-methylpyrrolidinone water or mixtures. The reaction temperatures are advantageously between −20° C. and +120° C. In general, the reactions can be carried out at ambient temperature. Suitable bases are, in particular pyridine, tertiary amines such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases.

O-alkoxy oxime derivatives of formula XII may also be prepared by sodium borohydride reduction of ester derivative of formula XXV in methanol. Ester derivates of formula XXV may be prepared by alkylation of oxime derivatives of formula XXVI with a compound $R_4$—Y, in which $R_4$ is as defined under formula IIA and Y represents a leaving group, such as halogen, mesylate or tosylate, in the presence of a base. Oxime derivative of formula XXVI may be obtained by nitrosation of di-ester derivatives of formula XXVII with an alkyl nitrite in the presence of sodium alkoholate as it is for example described in Organic Process Research & Development 2007, 11, 1069-1075 or Bioorganic & Medicinal Chemistry 13 (2005) 2783-2789. Knoevenagel condensation of a carbonyl compound of formula (IV) with dialkylmalonate, in which $R_{11}$ is $C_1$-$C_6$alkyl gave the compounds of formula XXVIII. Hydrogenation of the double bond of compound XXVIII gave the di-ester derivatives of formula XXVII.

Alternatively oxime ether derivatives of formula VIII may also be prepared by alkylation of oxime derivatives of formula IX with a compound $R_4$—Y, in which $R_4$ is as defined under formula IIA and Y represents a leaving group, such as halogen, mesylate or tosylate, in the presence of a base.

Alcohol compounds of formula X, XII and XIII can be converted to the corresponding fluoro compounds of formula VII, VIII and IIA, by nucleophilic fluorination with diethylaminosulfur trifluoride (DAST) and bis(2-methoxyethyl)aminosulfur trifluoride (Deoxofluor) as it is for example described in *Synthesis* 2002, Vol. 17, pp 2561-2578. Such fluorinations were most frequently conducted in anhydrous solvents such as $CH_2Cl_2$, $CHCl_3$, $CCl_3F$, hexane, isooctane and toluene from about −50° C. to about 100° C.

O-Alkylhydroxylamines of formula XIII and IIA may be prepared by the reduction of O-alkoxy oxime derivatives of formula XII and VIII. It will be appreciated by those skilled in the art that this reduction can be carried out with a number of different reducing agents.

Hydroxypenylpropanones of formula X, in which $R_6$, $R_7$ and $R_8$ are as defined under formula IIA, alternatively may be prepared as described in reaction scheme 2.

Scheme 2:

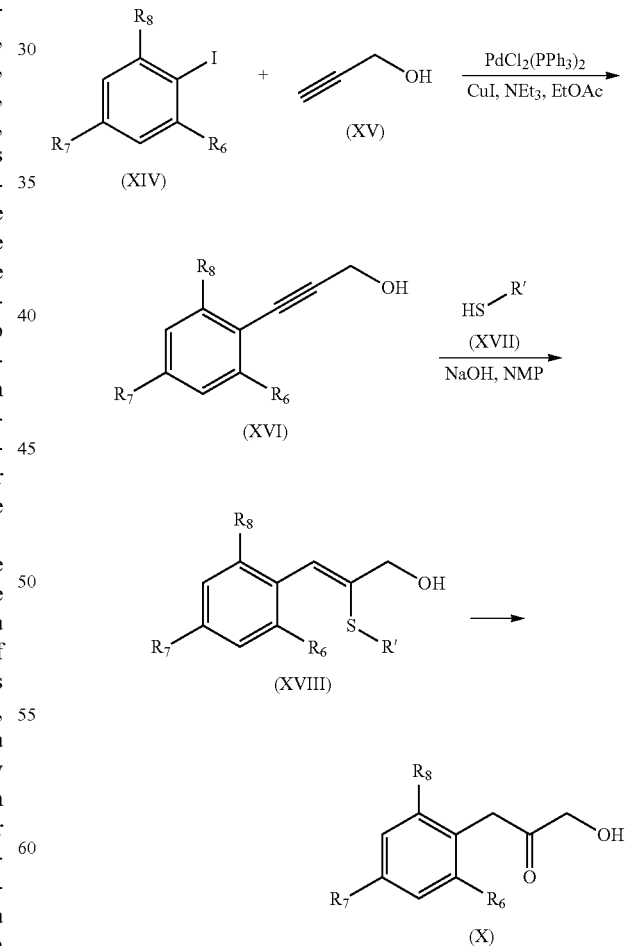

The Sonogashira reaction of aryl iodide XIV with propargyl alcohol XV can be performed in a solvent using a catalyst, for example, a transition metal catalyst, a metal halide, and a base. Suitable transition metal catalysts include Cu, Ni, Co, Fe and their donor complexes, for example, phosphine complexes and various salts, hydroxides, oxides, and organometallic derivatives thereof, such as the halides, carboxylates, triflates, tetrafluoroborates, hexafluorophosphates, hexafluoroantimonates, or sulfates and phosphine derivatives thereof, as well as combinations of the foregoing. In some embodiments, the catalyst is a transition metal catalyst, for example a palladium containing catalyst, such as Pd/C (with or without $PPh_3$), $PdCl_2(MeCN)_2$, $PdCl_2(PPh_3)_2$, $Pd(OAc)_2$, $PdCl_2$, $Pd(Ph_3P)_4$ and $Pd_2\,dba_3$. In some embodiments, the metal halide is a copper halide, for example, CuI. Suitable bases for the Sonogashira reaction include a wide variety of organic and inorganic bases, including but not limited to, trialkylamines such as triethylamine, aromatic bases such as imidazole, N-methylimidazole, pyridine, 2,6-lutidine, 2,4,6-collidine and di-tert-butylpyridines, 4-(dimethylamino)pyridine (DMAP), DBU, DBN, DABCO, N-alkylmorpholines, substituted piperidines, guanidines and anilines, quinoline and substituted quinolines, substituted and unsubstituted pyrrolidines and piperidines, metal hydrides, hydroxides, alkoxides, t-butoxides, oxides, carbonates, and the like. In some embodiments, the base is a trialkylamine, for example, triethylamine. The Sonogashira reaction can be performed at a wide range of temperatures, for example, from about −20° C. to about 250° C. A wide variety of solvents can be employed for the reaction as will be apparent to those of skill in the art. For example, suitable solvents include water; alcohols such as methanol, ethanol, n-propanol, isopropanol, butanols and alkoxyethanols; esters such as ethyl acetate, IPAC and BuOAc; hydrocarbons such as toluene or xylenes; chlorinated hydrocarbons such as dichloromethane, dichloroethane, chloroform and chlorobenzene; nitriles such as acetonitrile, propionitrile and benzonitrile; ketones such as acetone, MEK, MIBK and cyclohexanone; ethers such as diethyl ether, MTBE, THF, DME and DEM; other polar aprotic solvents such as formamide, DMF, DMA, NMP, DMPU, DMSO, and sulfolane or mixtures thereof.

A compound of formula XVI is reacted with a thiol of formula XVII in which R' represents a $C_1$-$C_{16}$alkyl alkyl group, in a solvent in the presence of a base to provide a thiopropenol of formula XVIII. Suitable bases for the reaction of compound XVI with a thiol include a wide variety of organic and inorganic bases, including but not limited to, trialkylamines, such as triethylamine, aromatic bases such as imidazole, N-methylimidazole, pyridine, 2,6-lutidine, 2,4,6-collidine and di-tert-butylpyridines, DMAP, DBU, DBN, DABCO, N-alkylmorpholines, substituted piperidines, guanidines and anilines, quinoline and substituted quinolines, substituted and unsubstituted pyrrolidines and piperidines, metal hydrides, hydroxides, alkoxides, t-butoxides, oxides, carbonates, and the like. In some embodiments, the base is a metal hydroxide, for example, sodium hydroxide.

Suitable solvents include, but are not limited to, water; alcohols such as methanol, ethanol, n-propanol, isopropanol, butanols and alkoxyethanols; esters such as EtOAc, IPAc and BuOAc; hydrocarbons such as toluene or xylenes; chlorinated hydrocarbons such as dichloromethane, dichloroethane, chloroform, chlorobenzene and ortho-dichlorobenzene; nitriles such as acetonitrile, propionitrile, benzonitrile and tolunitrile; ketones such as acetone, MEK, MIBK and cyclohexanone; ethers such as diethyl ether, MTBE, THF, DME and DEM; other polar aprotic solvents such as formamide, DMF, DMA, NMP, DMPU, DMSO, and sulfolane or mixtures thereof. In some embodiments, the solvent is a nitrogen containing organic solvent such as N-methylpyrrolidinone.

The reaction of the compound of formula XVI with a thiol of formula XVII can be performed at a wide range of temperatures, for example from about −20° C. to about 250° C. The same reaction can be performed under microwave conditions.

Hydroxyphenylpropanones of formula X, in which $R_6$, $R_7$ and $R_8$ are as defined under formula IIA, may be prepared by hydrolysis of thiopropenols of formula XVIII The hydrolysis of the compound of formula XVIII can be performed in an acidic medium. Suitable acids include but are not limited to, protic acids such as HCl, HBr, HI, sulfuric acid, phosphoric acid, and carboxylic acids such as acetic acid and trifluoroacetic acid. Suitable solvents include but are not limited to, water; alcohols such as methanol, ethanol, n-propanol, isopropanol, butanols and alkoxyethanols; esters such as EtOAc, IPAC and BuOAc; polar aprotic solvents such as formamide, DMF, DMA, NMP, DMPU, DMSO, and sulfolane or mixtures thereof. The hydrolysis of the compound of formula XVIII can be performed at a wide range of temperatures, for example from about 0° C. to about 200° C. The reaction can be performed under microwave conditions.

Fluorophenylpropanones of formula VII, in which $R_6$, $R_7$ and $R_8$ are as defined under formula IIA, alternatively may be prepared as described in reaction scheme 3.

Scheme 3:

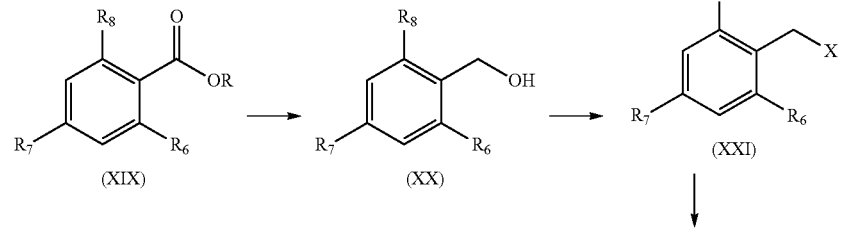

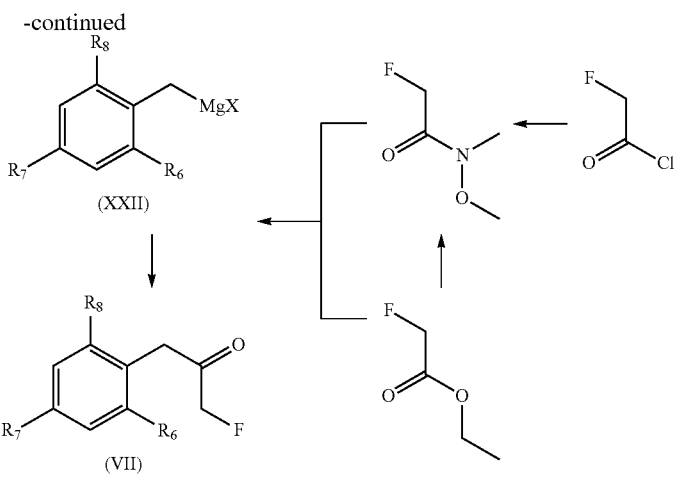

Benzylhalide derivatives of formula XXI, in which $R_6$, $R_7$ and $R_8$ are as defined under formula IIA and X represents a halogen, such as chloro, bromo or iodo can be prepared according to methods known in the art by reduction of acid derivatives of formula XIX into alcohol derivative of formula XX followed by the transformation into activated benzylic derivative of formula XXI, that can be further transformed into Grignard reagent XXII. Addition of fluoroacetic ester or the appropriate N-methyl-N-methoxyfluoroacetamide, prepared by standard methods from the corresponding fluoroacetic acid, ester or anhydride and N,O-dimethylhydroxylamine gave the b-fluoroketone VII.

Intermediates of the Formula IIB

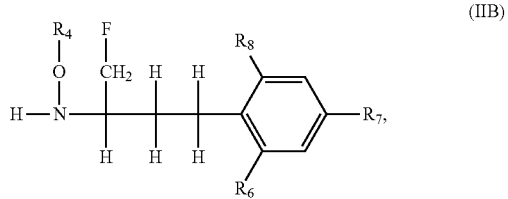

wherein $R_4$, $R_6$, $R_7$ and $R_8$ are as defined under formula I, may be prepared as described in reaction scheme 4.

Scheme 4:

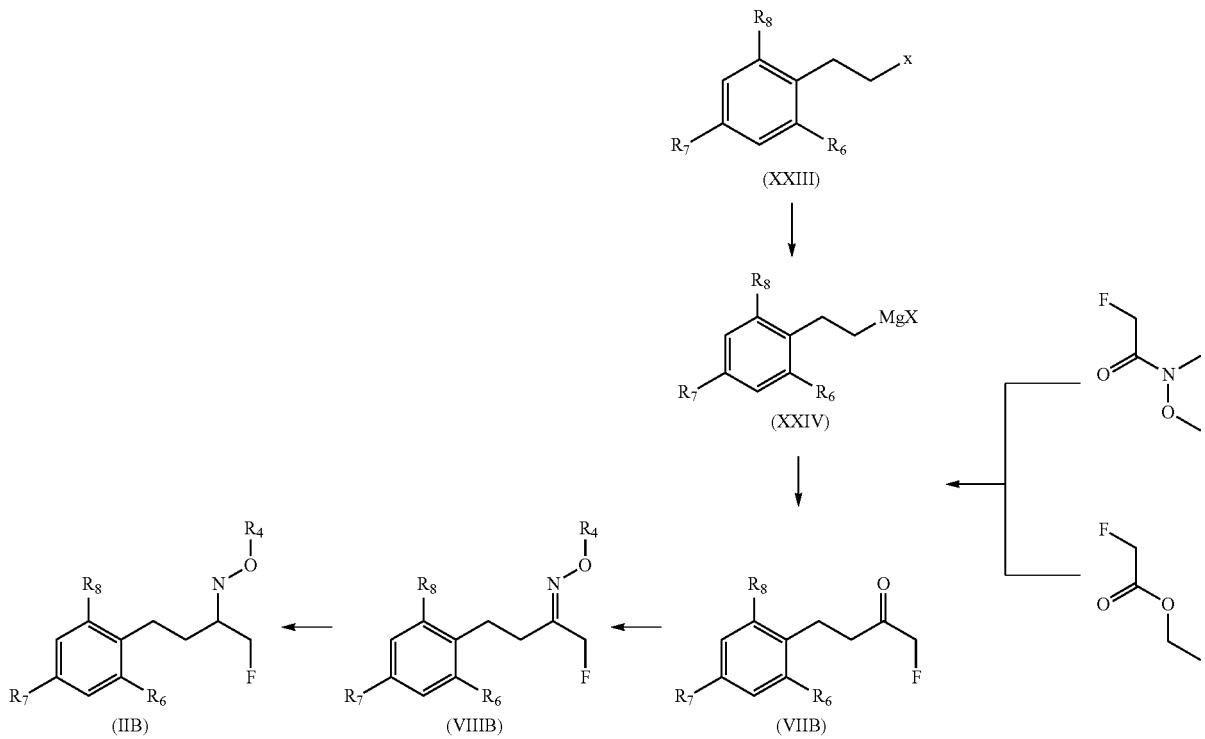

Grignard reagent derivatives of formula XXIV, in which $R_6$, $R_7$ and $R_8$ are as defined under formula IIA and X represents a halogen, such as chloro, bromo or iodo may be prepared from 2-haloethyl-benzene derivatives of formula XXIII and Magnesium, according to methods known in the art.

Dropwise addition of ethyl monofluoroacetate ester or the appropriate N-methyl-N-methoxyfluoroacetamide, prepared by standard methods from the corresponding fluoroacetic acid, ester or anhydride and N,O-dimethylhydroxylamine to a solution of the Grignard reagent derivatives of formula XXIV as described in *Journal of Fluorine Chemistry*, 35 (1987) 477-488 yield the b-fluoroketone derivative VIIB. Further oximation gave the corresponding oxime derivative VIIIB, followed by reduction to give the O-alkylhydroxylamines of formula IIB.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisams, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against *Septoria tritici*.

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB (b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as acitve ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as acitve ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as acitve ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

The compounds of formula (I), or a pharmaceutical salt thereof, described above may also have an advantageous spectrum of activity for the treatment and/or prevention of microbial infection in an animal. "Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection. According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*, those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-difluoromethyl-1-methyl-1H-pyrazole-4-carboxylic acid [2-(2,4-chloro-phenyl)-1-fluoromethyl-ethyl]-methoxy-amide (Compound 1.003)

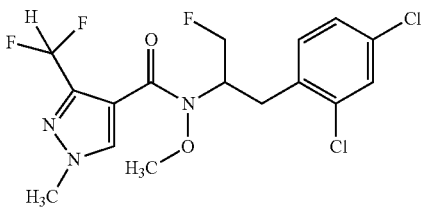 [SMILES: CON(C(=O)c1cn(C)nc1C(F)F)C(CF)Cc1ccc(Cl)cc1Cl]

To a stirred solution of N-[2-(2,4-dichlorophenyl)-1-fluoromethyl-ethyl]-O-methyl-hydroxylamine (0.21 g; 0.82 mmol), prepared as described in example P7c and triethylamine (0.13 ml; 0.90 mmol) in dichloromethane (1.9 ml) under nitrogen at 15° C. was added dropwise 3-difluoromethyl-1-methyl-1H-pyrazole-4-carbonyl chloride (0.16 g; 0.82 mmol). The reaction mixture was stirred at 24° C. for 16 h under nitrogen. The mixture was poured in water and extracted three times with dichloromethane. Combined organics were dried over sodium sulfate and the solvent was removed in vacuo. The crude was subject to flash chromatography (eluant: c-hexane/ethyl acetate 90:10 to 10:90) to afford 0.22 g (64% of theory) of 3-difluoromethyl-1-methyl-1H-pyrazole-4-carboxylic acid [2-(2,4-dichloro-phenyl)-1-fluoromethyl-ethyl]-methoxy-amide as a yellow oil.

$^1$H NMR (400 MHz, CHLOROFORM-d) δ ppm 3.02-3.31 (m, 2 H), 3.59 (s, 3 H), 3.96 (s, 3 H), 4.50-4.90 (m, 2 H), 4.75-4.87 (m, 1 H), 7.13 (t, J=55.0 Hz, 1 H), 7.14 (dd, J=8.4, 2.2 Hz, 1 H), 7.21 (d, J=8.1 Hz, 1 H), 7.37 (d, J=1.8 Hz, 1 H), 7.73 (br. s., 1 H)

MS [M+H]$^+$410/412.

Example P2

Preparation of 3-difluoromethyl-1-methyl-1H-pyrazole-4-carboxylic acid [1-fluoromethyl-2-(2,4,6-trichlorophenyl)-ethyl]-methoxy-amide (Compound 1.004)

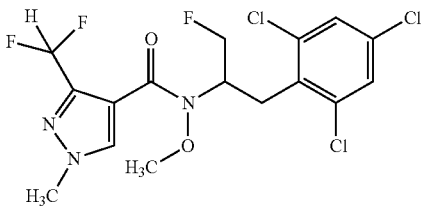 [SMILES: CON(C(=O)c1cn(C)nc1C(F)(F)F)C(CF)Cc1c(Cl)cc(Cl)cc1Cl]

To a stirred solution of N-[1-fluoromethyl-2-(2,4,6-trichlorophenyl)-ethyl]-O-methyl-hydroxylamine (8.4 g; 29 mmol), prepared as described in example P6f1 and triethylamine (5.0 ml; 35 mmol) in dichloromethane (70 ml) under nitrogen at 0° C. was added dropwise 3-difluoromethyl-1-methyl-1H-pyrazole-4-carbonyl chloride (6.0 g; 29 mmol). The reaction mixture was stirred at 24° C. for 16 h under nitrogen. The mixture was washed with 1M sodium hydroxide (40 ml) and 1M hydrochloric acid (40 ml). Organics were dried over sodium sulfate. The solvent was removed in vacuo to afford 13.6 g of a sticky oil which was subject to flash chromatography (eluant: c-hexane/ethyl acetate 90:10 to 70:30) to afford 10.7 g (82% of theory) of 3-difluoromethyl-1-methyl-1H-pyrazole-4-carboxylic acid [1-fluoromethyl-2-(2,4,6-trichlorophenyl)-ethyl]-methoxy-amide as a white solid (melting point: 117-118° C.).

$^1$H NMR (400 MHz, CHLOROFORM-d) δ ppm 3.20-3.53 (m, 4 H), 3.68 (s, 3 H), 3.99 (s, 3 H), 4.43-5.00 (m, 4 H), 4.77-4.89 (m, 1 H), 7.17 (t, J=53.0 Hz, 1 H), 7.32 (s, 2 H), 7.85 (s, 1 H)

MS [M+H]$^+$444/446/448.

Example P3

Preparation of 1-methyl-3-trifluoromethyl-1H-pyrazole-4-carboxylic acid [1-fluoromethyl-2-(2,4,6-trichlorophenyl)-ethyl]-methoxy-amide (Compound 3.004)

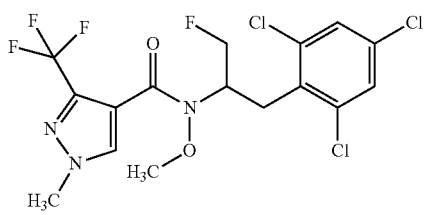

To a stirred solution of N-[1-fluoromethyl-2-(2,4,6-trichlorophenyl)-ethyl]-O-methyl-hydroxylamine (0.20 g; 0.70 mmol), prepared as described in example P6f2 and triethylamine (0.12 ml; 0.84 mmol) in dichloromethane (1.6 ml) under nitrogen at 4° C. was added dropwise 1-methyl-3-trifluoromethyl-1H-pyrazole-4-carbonyl chloride (0.15 g; 0.70 mmol). The reaction mixture was stirred at 24° C. for 3 h under nitrogen. Triethylamine (0.19 ml; 1.4 mmol) was added again to the mixture followed by 1-methyl-3-trifluoromethyl-1H-pyrazole-4-carbonyl chloride (74 mg; 0.35 mmol). The mixture was stirred at 24° C. for 18 h. The mixture was washed with 1M sodium hydroxide (20 ml), 1M hydrochloric acid (20 ml) and brine (20 ml). Organics were dried over sodium sulfate. The solvent was removed in vacuo. The crude was subject to flash chromatography (eluant: c-hexane/ethyl acetate 90:10 to 50:50) to afford 0.17 g (51% of theory) of 1-methyl-3-trifluoromethyl-1H-pyrazole-4-carboxylic acid [1-fluoromethyl-2-(2,4,6-trichlorophenyl)-ethyl]-methoxy-amide as a yellow solid (melting point: 131-133° C.).

$^1$H NMR (400 MHz, CHLOROFORM-d) δ ppm 3.22-3.51 (m, 2 H), 3.63 (br. s., 3 H), 3.98 (s, 3 H), 4.39-4.98 (m, 2 H), 4.72-4.85 (m, 1 H), 7.33 (s, 2 H), 7.75 (br. s., 1 H)

MS [M+H]$^+$462/464/466.

Example P4

Preparation of 5-fluoro-1,3-dimethyl-1H-pyrazole-4-carboxylic acid [1-fluoromethyl-2-(2,4,6-trichlorophenyl)-ethyl]-methoxy-amide (Compound 5.004)

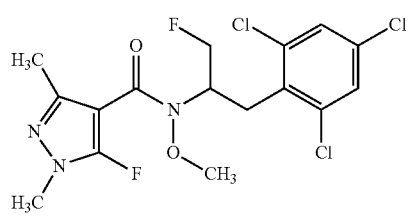 [SMILES: CON(C(=O)c1c(C)nn(C)c1F)C(CF)Cc1c(Cl)cc(Cl)cc1Cl]

To a stirred solution of N-[1-fluoromethyl-2-(2,4,6-trichloro-phenyl)-ethyl]-O-methylhydroxylamine (0.20 g; 0.70 mmol), prepared as described in example P6f2 in chlorobenzene (3.8 ml) was added 2,6-lutidine (85 µl; 0.74 mmol) and 5-fluoro-1,3-dimethyl-1H-pyrazole-4-carbonyl fluoride (0.11 g; 0.70 mmol). The yellow solution was stirred at reflux (130° C.) for 22 hours. The dark brown solution was dissolved in dichloromethane (20 ml), washed with 1 M sodium hydroxide solution (20 ml), 1 M hydrochloric acid solution (20 ml), brine (20 ml), dried over sodium sulfate and evaporated under reduced pressure. The crude was subject to flash chromatography (eluant: c-hexane/ethyl acetate 9:1 to 7:3) to afford 20 mg (7% of theory) of 5-fluoro-1,3-dimethyl-1H-pyrazole-4-carboxylic acid [1-fluoromethyl-2-(2,4,6-trichlorophenyl)-ethyl]-methoxy-amide as a brown oil.

$^1$H NMR (400 MHz, CHLOROFORM-d) δ ppm 2.25 (s, 3 H), 3.13-3.46 (m, 2 H), 3.67 (s, 3 H), 3.69 (s, 3 H), 4.38-4.97 (m, 3 H), 7.32 (s, 2 H)

MS [M+H]$^+$426/428/430.

Example P5

Preparation of 3-difluoromethyl-1-methyl-1H-pyrazole-4-carboxylic acid [3-(4-chloro-phenyl)-1-fluoromethyl-propyl]-methoxy-amide (Compound 2.002)

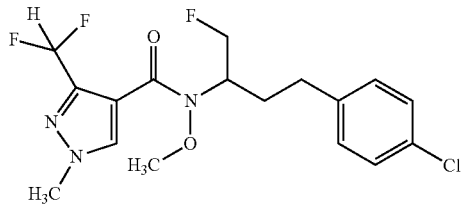 [SMILES: CON(C(=O)c1cn(C)nc1C(F)F)C(CF)CCc1ccc(Cl)cc1]

To a stirred solution of N-[3-(4-chlorophenyl)-1-fluoromethyl-propyl]-O-methyl-hydroxylamine (60 mg; 0.26 mmol), prepared as described in example P8c and triethylamine (0.05 ml; 0.31 mmol) in dichloromethane (1 ml) under nitrogen was added drop wise 3-difluoromethyl-1-methyl-1H-pyrazole-4-carbonyl chloride (51 mg; 0.26 mmol). The reaction mixture was stirred at 24° C. for 16 hours under nitrogen. The mixture was washed with 1M sodium hydroxide (20 ml), 1M hydrochloric acid (20 ml) and brine (20 ml). Organics were dried over sodium sulfate and evaporated under reduced pressure. The crude was subject to flash chromatography (eluant: c-hexane/ethyl acetate 90:10 to 70:30) to afford 67 mg (66% of theory) of 3-difluoromethyl-1-methyl-1H-pyrazole-4-carboxylic acid [3-(4-chloro-phenyl)-1-fluoromethyl-propyl]-methoxy-amide as a clear oil.

$^1$H NMR (400 MHz, CHLOROFORM-d) δ ppm 1.78-1.94 (m, 1 H), 2.11-2.28 (m, 1 H), 2.55-2.78 (m, 2 H), 3.73 (s, 3 H), 3.99 (s, 3 H), 4.38-4.80 (m, 3 H), 7.10 (d, J=8.1 Hz, 2 H), 7.23 (t, J=52.0 Hz, 1 H), 7.23 (d, J=8.4 Hz, 2 H), 7.84 (br. s., 1 H). MS [M+H]$^+$390/392.

Example P6

Preparation of N-[1-fluoromethyl-2-(2,4,6-trichlorophenyl)-ethyl]-O-methyl-hydroxylamine a) Preparation of 2-nitro-3-(2,4,6-trichloro-phenyl)-prop-2-en-1-ol

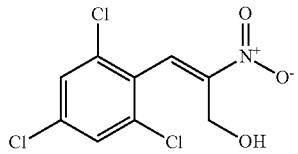 [SMILES: O=[N+]([O-])/C(=C/c1c(Cl)cc(Cl)cc1Cl)CO]

In a sulfonation flask equipped with a mechanical stirrer, a condenser, a dropping funnel and a thermometer under argon, 2,4,6-trichlorobenzaldehyde (74.8 g; 357 mmol) was suspended in glacial acetic acid (500 ml). 2-nitroethanol (182 ml; 2.46 mol) was added dropwise at 24° C. followed by ammonium acetate (66.1 g; 875 mmol). The mixture was stirred for 2.5 hours at 90° C. The orange suspension turned slowly to a dark brown solution during reaction. Most of the acetic acid was removed under reduced pressure and the residue poured on 1.6 l of ice-water to give a red brown emulsion which was extracted with ethyl acetate (3×600 ml). Combined organics were washed with brine, dried over sodium sulfate and evaporated under reduced pressure to give the crude as dark brown oil (307 g) which was subject to flash chromatography (eluant: c-hexane/ethyl acetate 9:1). 62 g (62% of theory) of 2-nitro-3-(2,4,6-trichloro-phenyl)-prop-2-en-1-ol was obtained as a red brown oil.

$^1$H NMR (400 MHz, CHLOROFORM-d) δ ppm 2.43 (t, J=7.3 Hz, 1 H), 4.42 (d, J=7.3 Hz, 2 H), 7.45 (s, 2 H), 7.84 (s, 1 H).

b1) Preparation of 1-hydroxy-3-(2,4,6-trichloro-phenyl)-propan-2-one

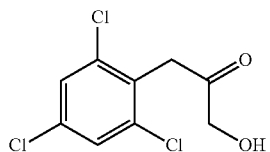 [SMILES: O=C(CO)Cc1c(Cl)cc(Cl)cc1Cl]

In a sulfonation flask equipped with a mechanical stirrer, a condenser, a dropping funnel and a thermometer under argon flux, 2-nitro-3-(2,4,6-trichloro-phenyl)-prop-2-en-1-ol (62 g; 220 mmol) was dissolved at 23° C. in methanol (600 ml) to give a dark red solution. Water (250 ml) was added (a fine suspension appeared) followed by hydrochloric acid, 32% (125 ml; 1500 mmol) dropwise (during 10 min) (temperature rose to 33° C.) and finally iron powder (28 g; 506 mmol) portionwise (temperature rose to 35° C.). The reaction mixture was stirred at 73° C. (reflux) for 4 h. Methanol was removed under reduced pressure and the resulting solution filtered through celite. Mother liquors were poured in water (400 ml) and brine (400 ml) which was extracted four times with ethyl acetate (300 ml). Red organics and green aqueous obtained. Combined organics were washed with brine (500 ml), dried over sodium sulfate and evaporated under reduced pressure to give the crude as red oil (66 g) which was subject to flash chromatography (eluant: c-hexane/ethyl acetate 4:1). 35 g (63% of theory) of 1-hydroxy-3-(2,4,6-trichloro-phenyl)-propan-2-one was obtained as a grey solid (melting point: 75-80° C.).

$^1$H NMR (400 MHz, CHLOROFORM-d) δ ppm 3.02 (br. s, 1 H), 4.07 (s, 2 H), 4.39 (s, 2 H), 7.38 (s, 2 H)
MS [M−H]$^-$251/253/255.

b2) Preparation of 1-hydroxy-3-(2,4,6-trichloro-phenyl)-propan-2-one

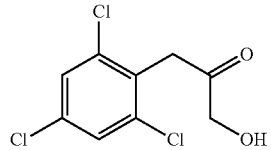

To an emulsion of dodecylsulfanyl-3-(2,4,6-trichloro-phenyl)-prop-2-en-1-ol (0.82 g; 1.9 mmol), prepared as described in example P61 in methanol (3 ml) was added dropwise 30% sulfuric acid (1.5 ml; 5.6 mmol). The temperature increased from 23° C. until 28° C. The mixture was heated at 60° C. for 5 h. Dioxane (2 ml) was added and reaction was stirred at 60° C. for 18 h. The biphasic mixture was transferred in a sealed microwave vial and heated at 80° C. for 10 min and at 100° C. for 10 min. The mixture obtained was poured in water and was extracted once with ethyl acetate. Organic layer was washed three times with water, dried over sodium sulfate and evaporated. The crude oil obtained was subject to flash chromatography (eluant: c-hexane/ethyl acetate 4:1). 80 mg (18% of theory) of 1-hydroxy-3-(2,4,6-trichloro-phenyl)-propan-2-one was obtained as a light yellow solid.

$^1$H NMR (400 MHz, CHLOROFORM-d) δ ppm 3.02 (br. s, 1 H), 4.07 (s, 2 H), 4.39 (s, 2 H), 7.38 (s, 2 H)
MS [M−H]$^-$251/253/255.

c) Preparation of 1-hydroxy-3-(2,4,6-trichloro-phenyl)-propan-2-one O-methyl-oxime

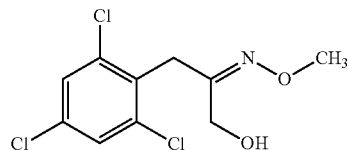

To a stirred solution of 1-hydroxy-3-(2,4,6-trichloro-phenyl)-propan-2-one (30 g; 118 mmol) in methanol (240 ml) was added pyridine (15 ml; 189 mmol) followed by a portionwise addition of methoxyamine hydrochloride (15 g; 178 mmol). The reaction mixture was stirred at 24° C. for 18 h under nitrogen. Methanol was removed under reduced pressure, the residue poured in water (300 ml) and 1N hydrochloric acid was added (100 ml). The solution was extracted with dichloromethane (3×150 ml). Combined organic layers were washed with water (300 ml) and dried over sodium sulfate. The solvent was removed in vacuo to afford 33 g (99% of theory) of 1-hydroxy-3-(2,4,6-trichloro-phenyl)-propan-2-one O-methyl-oxime (isomers E/Z 1:1) as a brown oil.

$^1$H NMR (400 MHz, CHLOROFORM-d) δ ppm 2.42 (br. s., 2 H), 3.75 (s, 3 H), 3.90 (s, 2 H), 3.92 (s, 2 H), 3.95 (s, 3 H), 4.02 (s, 2 H), 4.37 (s, 2 H), 7.33 (s, 2 H), 7.35 (s, 2 H)

MS [M+H]$^+$282/284/286.

d) Preparation of 1-fluoro-3-(2,4,6-trichloro-phenyl)-propan-2-one O-methyl-oxime

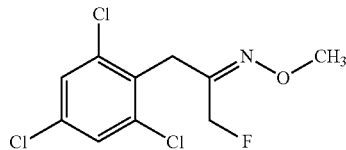 [SMILES: CO/N=C(\CF)Cc1c(Cl)cc(Cl)cc1Cl]

To a stirred brown suspension of 1-hydroxy-3-(2,4,6-trichloro-phenyl)-propan-2-one O-methyl-oxime (33 g; 117 mmol) in dichloromethane (235 ml) at −20° C. under nitrogen was added dropwise a solution of diethylaminosulfur trifluoride (16 ml; 123 mmol) in dichloromethane (62 ml). During addition, temperature rose to −10° C. The mixture turned to a brown orange solution which was allowed to warm at 20° C. and was stirred for 2 hours. The organic solution was washed with saturated hydrogen carbonate solution (200 ml), 1N hydrochloric acid (200 ml), brine (200 ml) and dried over sodium sulfate. The solvent was removed in vacuo to afford 37 g (110% of theory) of crude 1-fluoro-3-(2,4,6-trichloro-phenyl)-propan-2-one O-methyl-oxime (isomers E/Z) as a brown oil.

Isomer 1:

$^1$H NMR (400 MHz, CHLOROFORM-d) δ ppm 3.92 (s, 3 H), 4.07 (d, J=2.9 Hz, 2 H), 4.66 (d, J=47.3 Hz, 2 H), 7.35 (s, 2 H)

Isomer 2:

$^1$H NMR (400 MHz, CHLOROFORM-d) δ ppm 3.70 (s, 3 H), 3.97 (s, 2 H), 5.28 (d, J=47.3 Hz, 2 H), 7.33 (s, 2 H)

MS [M+H]$^+$284/286/288.

e) Characterisation of 2-Methoxyamino-3-(2,4,6-trichlorophenyl)-propan-1-ol

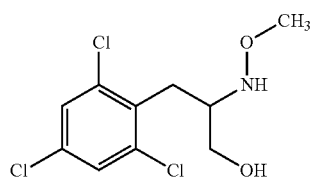 [SMILES: CONC(CO)Cc1c(Cl)cc(Cl)cc1Cl]

$^1$H NMR (400 MHz, CHLOROFORM-d) δ ppm 2.22 (br. s., 1 H), 2.94-3.20 (m, 2 H), 3.36 (qd, J=6.7, 4.2 Hz, 1 H), 3.55 (s, 3 H), 3.63-3.71 (m, 2 H), 5.80 (br. s., 1 H), 7.33 (s, 2 H)

MS [M+H]$^+$284/286/288.

f1) Preparation of N-[1-fluoromethyl-2-(2,4,6-trichlorophenyl)-ethyl]-O-methyl-hydroxylamine (Compound 7.004)

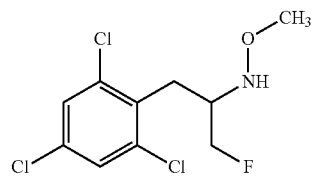 [SMILES: CONC(CF)Cc1c(Cl)cc(Cl)cc1Cl]

To a stirred solution of 1-fluoro-3-(2,4,6-trichloro-phenyl)-propan-2-one, O-methyl-oxime (33 g; 117 mmol) in acetic acid (240 ml) at 24° C. was added sodium cyanoborohydride (22 g; 361 mmol) portionwise (gas release and temperature increase to 35° C. was observed). The solution was stirred at 24° C. for 18 h. Most of the acetic acid was removed in vacuo. The mixture was diluted with dichloromethane and was washed with basic aqueous solution (ice water+NaOH 32% solution pH=14). Aqueous layer was extracted three times with dichloromethane. Organics were combined, washed once with brine, dried over sodium sulfate and evaporated. The crude was subject to column chromatography (c-hexane/ethyl acetate 95:5) to afford 19 g of a mixture of N-[1-fluoromethyl-2-(2,4,6-trichlorophenyl)-ethyl]-O-methyl-hydroxylamine and 1-fluoro-3-(2,4,6-trichloro-phenyl)-propan-2-one O-methyl-oxime. The oil obtained (19 g) was dissolved in acetic acid (135 ml) at 24° C. and sodium cyanoborohydride (6.3 g; 100 mmol) was added portionwise. The solution was stirred at 24° C. for 18 h. Most of the acetic acid was removed in vacuo. The mixture was diluted with dichloromethane and was washed with basic aqueous solution (ice water+NaOH 32% solution pH=14). Aqueous layer was extracted three times with dichloromethane. Organics were combined, washed once with brine, dried over sodium sulfate and evaporated. The crude was subject to column chromatography (c-hexane/ethyl acetate 95:5) to afford 8.6 g (25% of theory) of N-[1-fluoromethyl-2-(2,4,6-trichlorophenyl)-ethyl]-O-methyl-hydroxylamine as a yellow oil.

$^1$H NMR (400 MHz, CHLOROFORM-d) δ ppm 3.02-3.22 (m, 2 H), 3.44-3.52 (m, 1 H), 3.53 (s, 3 H), 4.48 (ddd, J=47.0, 5.1, 2.2 Hz, 2 H), 5.76 (br. s, 1 H), 7.34 (s, 2 H)

MS [M+H]$^+$286/288/290.

f2) Preparation of N-[1-fluoromethyl-2-(2,4,6-trichlorophenyl)-ethyl]-O-methyl-hydroxylamine

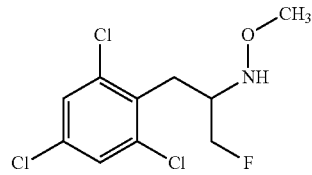 [SMILES: CONC(CF)Cc1c(Cl)cc(Cl)cc1Cl]

To a stirred thick suspension of 2-methoxyamino-3-(2,4,6-trichloro-phenyl)-propan-1-ol (1.0 g; 3.5 mmol) in dichloromethane (7.0 ml) at −16° C. under nitrogen was added dropwise a solution of diethylaminosulfur trifluoride (0.46 ml; 3.5 mmol) in dichloromethane (2.0 ml). During addition temperature rose to −12° C. The mixture turned to a brown orange solution which was allowed to warm at 20° C. and was stirred for 2 h. The organic solution was washed with saturated hydrogen carbonate solution (gas release), 1N hydrochloric acid, brine and dried over sodium sulfate. The solvent was removed in vacuo. The crude material was subject to flash column chromatography (eluant: cyclohexan/ethyl acetate 95:5) to afford 0.43 g (43% of theory) of N-[1-fluoromethyl-2-(2,4,6-trichlorophenyl)-ethyl]-O-methyl-hydroxylamine as a yellow oil.

$^1$H NMR (400 MHz, CHLOROFORM-d) δ ppm 3.02-3.22 (m, 2 H), 3.44-3.52 (m, 1 H), 3.53 (s, 3 H), 4.48 (ddd, J=47.0, 5.1, 2.2 Hz, 2 H), 5.76 (br. s, 1 H), 7.34 (s, 2 H)

MS [M+H]$^+$286/288/290.

g) Preparation of 1,3,5-trichloro-2-iodo-benzene

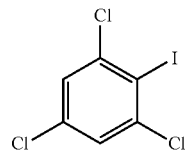

To a solution of paratoluene sulfonic acid monohydrate (14.5 g; 76.4 mmol) in acetonitrile (100 ml) was added the 2,4,6-trichloroaniline (5.0 g; 25.5 mmol). The resulting white suspension was cooled to 10-15° C. and to this was added, gradually a solution of sodium nitrite (3.5 g; 51.0 mmol) and potassium iodide (10.6 g; 63.6 mmol) in water (15 ml), the suspension became dark brown, thick and gas release was observed. The thick mixture was stirred for 10 min at 10° C. and then temperature was allowed to increase to 20° C. The solution obtained was stirred for 1 h. The solution was poured in water, 1M sodium hydrogen carbonate solution was added (pH adjusted to 9-10) and 2M solution of sodium thiosulfate was added. The mixture was extracted three times with dichloromethane. Organics were combined, dried over sodium sulfate and the solvent was removed in vacuo to provide a resin which was subject to flash column chromatography (eluant: c-hexane). 6.3 g (80% of theory) of 1,3,5-trichloro-2-iodo-benzene was obtained as a white solid.

$^1$H NMR (400 MHz, CHLOROFORM-d) δ ppm 7.37 (s, 2 H)

h) Preparation of 3-(2,4,6-trichloro-phenyl)-prop-2-yn-1-ol

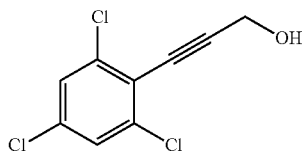 [SMILES: OCC#Cc1c(Cl)cc(Cl)cc1Cl]

To a microwave vial were added propargyl alcohol (0.19 ml; 3.3 mmol), 1,3,5-trichloro-2-iodo-benzene (0.50 g; 1.6 mmol), N,N-dimethylformamide (6 ml), triethylamine (4 ml), bis(triphenylphosphine) palladium(II) chloride (0.11 g; 0.16 mmol) and copper iodide (31 mg; 0.16 mmol). The mixture was degassed under argon. The orange solution was heated in the microwave at 120° C. during 25 min. The mixture obtained was poured in brine and extracted three times with dichloromethane. Organic were combined, dried over sodium sulfate and evaporated under reduced pressure to provide the crude which was subject to flash chromatography (eluant: c-hexane/ethyl acetate 8:2). 290 mg (75% of theory) of 3-(2,4,6-trichloro-phenyl)-prop-2-yn-1-ol was obtained as a yellow solid.

$^1$H NMR (400 MHz, CHLOROFORM-d) δ ppm 1.77 (t, J=6.2 Hz, 1 H), 4.60 (d, J=6.2 Hz, 2 H), 7.35 (s, 2 H)

i) Preparation of dodecylsulfanyl-3-(2,4,6-trichloro-phenyl)-prop-2-en-1-ol

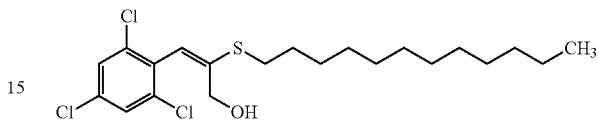

To a solution of 3-(2,4,6-trichloro-phenyl)-prop-2-yn-1-ol (1.0 g; 4.2 mmol) in N-methyl-2-pyrrolidone (10 ml) and ethyl acetate (2 ml) at 2° C. was added sodium hydroxide (grind to powder) (0.19 g; 4.7 mmol). At 5° C. was added dropwise dodecanethiol (1.4 ml; 6.0 mmol). The reaction mixture was allowed to warm at 22° C. and was stirred for 30 min. The mixture was poured in water and ethyl acetate was added. Organic layer was washed three times with brine, dried over sodium sulfate and evaporated. The crude oil obtained was subject to flash chromatography (eluant: c-hexane/ethyl acetate 99:1 to 80:20) to afford 0.60 g (32% of theory) of dodecylsulfanyl-3-(2,4,6-trichloro-phenyl)-prop-2-en-1-ol as a yellow oil.

$^1$H NMR (400 MHz, CHLOROFORM-d) δ ppm 0.88 (t, J=6.6 Hz, 3 H), 1.15-1.32 (m, 18 H), 1.41-1.53 (m, 2 H), 1.92 (t, J=6.2 Hz, 1 H), 2.58-2.68 (m, 2 H), 4.41 (d, J=5.1 Hz, 2 H), 6.61 (s, 1 H), 7.35 (s, 2 H)

Example P7

Preparation of N-[2-(2,4-dichlorophenyl)-1-fluoromethyl-ethyl]-O-methyl-hydroxylamine a) Preparation of 1-(2,4-dichloro-phenyl)-3-fluoro-propan-2-one

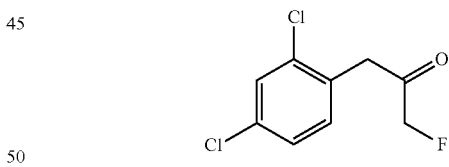

To a stirred solution of ethyl fluoroacetate (0.33 ml; 3.3 mmol) in dry diethyl ether (3.3 ml) under argon at −76° C. was added dropwise a 0.25 M solution of 2,4-dichlorobenzylmagnesium chloride in diethyl ether (20 ml; 5 mmol). The suspension was stirred at −60° C. during 5 h. The mixture was poured in ammonium chloride sat. solution and extracted three times with diethylether. Organics were combined, dried over sodium sulfate and evaporated to a resin which was subject to flash chromatography (eluant: c-hexane/ethyl acetate 99:1 to 70:30) to afford 0.36 g (49% of theory) of 1-(2,4-dichloro-phenyl)-3-fluoro-propan-2-one as a pale yellow solid (melting point: 48-52° C.).

$^1$H NMR (400 MHz, CHLOROFORM-d) δ ppm 3.99 (d, J=2.6 Hz, 2 H), 4.93 (d, J=47.3 Hz, 2 H), 7.16 (d, J=8.1 Hz, 1 H), 7.25 (dd, J=8.1, 2.2 Hz, 1 H), 7.43 (d, J=2.2 Hz, 1 H)

MS [M−H]$^-$219/221.

b) Preparation of 1-(2,4-dichloro-phenyl)-3-fluoro-propan-2-one O-methyl-oxime

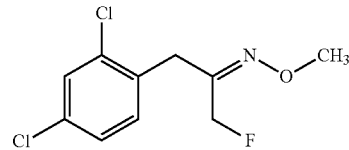

To a stirred solution of 1-(2,4-dichloro-phenyl)-3-fluoro-propan-2-one (0.34 g; 1.5 mmol) in methanol (3 ml) was added pyridine (0.4 ml; 4.9 mmol) followed by a portionwise addition of methoxyamine hydrochloride (0.41 g; 4.9 mmol). The reaction mixture was stirred for 16 hours at 23° C. The mixture was washed with water (5 ml), the aqueous layer was extracted with dichloromethane (3×5 ml) and dried over sodium sulfate. The solvent was removed in vacuo to afford 0.40 g (100% of theory) of crude 1-(2,4-dichloro-phenyl)-3-fluoro-propan-2-one O-methyl-oxime (isomers E/Z) as a yellow oil.

Isomer 1:

$^1$H NMR (400 MHz, CHLOROFORM-d) δ ppm 3.86 (s, 2 H), 3.94 (s, 3 H), 4.78 (d, J=45.8 Hz, 2 H), 7.13-7.22 (m, 2 H), 7.39 (s, 1 H)

Isomer 2:

$^1$H NMR (400 MHz, CHLOROFORM-d) δ ppm 3.75 (d, J=2.6 Hz, 2 H), 3.84 (s, 3 H), 5.20 (d, J=47.3 Hz, 2 H), 7.13-7.22 (m, 2 H), 7.40 (s, 1 H)

MS [M+H]$^+$250/252.

c) Preparation of N-[2-(2,4-dichlorophenyl)-1-fluoromethyl-ethyl]-O-methyl-hydroxylamine (Compound 7.003)

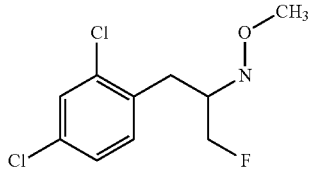

To a stirred solution of 1-(2,4-dichloro-phenyl)-3-fluoro-propan-2-one O-methyl-oxime (0.36 g; 1.4 mmol) in acetic acid (2.8 ml) was added portionwise sodium cyanoborohydride 95% (0.18 g; 2.8 mmol). The mixture was stirred for 18 hours at 23° C. Most of acetic acid was removed under reduced pressure. The residue was poured in water (10 ml) and was extracted with dichloromethane (3×10 ml). Combined organics were dried over sodium sulfate and solvent was removed in vacuo. The crude was subject to flash chromatography (eluant: c-hexane/ethyl acetate 95:5) to afford 0.27 g (75% of theory) of N-[2-(2,4-dichlorophenyl)-1-fluoromethyl-ethyl]-O-methyl-hydroxylamine as a yellow oil.

$^1$H NMR (400 MHz, CHLOROFORM-d) δ ppm 2.80-3.00 (m, 2 H), 3.30-3.45 (m, 1 H), 3.54 (s, 3 H), 4.30-4.60 (m, 2 H), 5.70 (s, 1 H), 7.18-7.25 (m, 2 H), 7.40 (s, 1 H)

MS [M+H]$^+$252/254.

Example P8

Preparation of N-[2-(2,4-dichlorophenyl)-1-fluoromethyl-ethyl]-O-methyl-hydroxylamine a) Preparation of 4-(4-chloro-phenyl)-1-fluoro-butan-2-one

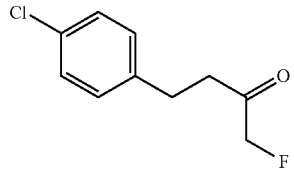 [SMILES: O=C(CF)CCc1ccc(Cl)cc1]

To a stirred solution of ethyl fluoroacetate (0.59 ml; 6.0 mmol) in tetrahydrofuran (6 ml) under nitrogen at −76° C. was added dropwise a 0.5 M solution of 4-chlorophenethylmagnesium bromide in tetrahydrofuran (10 ml; 5.0 mmol). The suspension obtained was stirred at −50° C. during 5 h. The mixture was poured in ammonium chloride sat. solution (20 ml) and extracted with dichloromethane (3×20 ml). Combined organics were dried over sodium sulfate and evaporated. The crude obtained was subject flash chromatography (eluant: c-hexane/ethyl acetate 95:5) to afford 0.13 g (18% of theory) of 4-(4-chloro-phenyl)-1-fluoro-butan-2-one as a yellow oil.

$^1$H NMR (400 MHz, CHLOROFORM-d) δ ppm 2.83-2.97 (m, 4 H), 4.77 (d, J=47.7 Hz, 2 H), 7.13 (d, J=8.4 Hz, 2 H), 7.26 (d, J=8.4 Hz, 2 H)

MS [M−H]$^-$199/201.

b) Preparation of 4-(4-chloro-phenyl)-1-fluoro-butan-2-one O-methyl-oxime

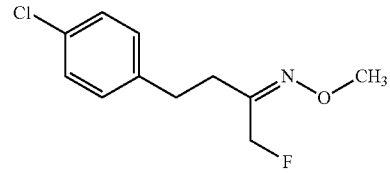

To a stirred suspension of 4-(4-chloro-phenyl)-1-fluoro-butan-2-one (0.13 g; 0.62 mmol) in methanol (1.3 ml) was added pyridine (80 μl; 0.99 mmol) followed by a portion wise addition of methoxyamine hydrochloride (78 mg; 0.93 mmol). The reaction mixture was stirred for 16 h at 23° C. The mixture was poured in 1 N hydrochloric acid (5 ml), extracted with dichloromethane (3×3 ml) and dried over sodium sulfate. The solvent was removed in vacuo to afford 0.13 g (94% of theory) of 4-(4-chloro-phenyl)-1-fluoro-butan-2-one O-methyl-oxime (mixture of E/Z-isomers) as a yellow oil.

Isomer 1:

$^1$H NMR (400 MHz, CHLOROFORM-d) δ ppm 2.63-2.73 (m, 2 H), 2.76-2.90 (m, 2 H), 3.88 (s, 3 H), 4.75 (d, J=47.0 Hz, 2 H), 7.11-7.18 (m, 2 H), 7.23-7.28 (m, 2 H)

Isomer 2:

$^1$H NMR (400 MHz, CHLOROFORM-d) δ ppm 2.56-2.64 (m, 2 H), 2.78-2.89 (m, 2 H), 3.81 (s, 3 H), 5.22 (d, J=48.0 Hz, 2 H), 7.11-7.18 (m, 2 H), 7.23-7.28 (m, 2 H)

MS [M+H]$^+$230/232.

c) Preparation of N-[3-(4-chlorophenyl)-1-fluoromethyl-propyl]-O-methyl-hydroxylamine (Compound 8.002)

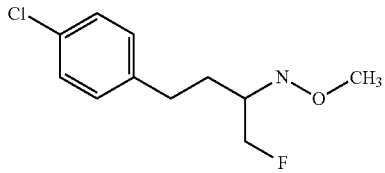

To a stirred solution 4-(4-chloro-phenyl)-1-fluoro-butan-2-one O-methyl-oxime (mixture of E/Z-isomers) (0.13 g; 0.58 mmol) in acetic acid (1.2 ml) was added portion wise sodium cyanoborohydride 95% (75 mg; 1.2 mmol). The mixture was stirred for 18 hours at 23° C. Most of acetic acid was removed under reduced pressure. The residue was poured in 1 M sodium hydroxide solution (5 ml) and was extracted with dichloromethane (3×2 ml).

Combined organics were dried over sodium sulfate and solvent was removed in vacuo. The crude was subject to flash chromatography (eluant: c-hexane/ethyl acetate 95:5) to afford 60 mg (45% of theory) of N-[3-(4-chlorophenyl)-1-fluoromethyl-propyl]-O-methyl-hydroxylamine as a yellow oil.

$^1$H NMR (400 MHz, CHLOROFORM-d) δ ppm 1.63-1.86 (m, 2 H), 2.64-2.81 (m, 2 H), 2.98-3.11 (m, 1 H), 3.55 (s, 3 H), 4.33-4.58 (m, 2 H), 5.69 (br. s, 1 H), 7.13 (d, J=8.1 Hz, 2 H), 7.26 (d, J=8.1 Hz, 2 H)

MS [M+H]$^+$232/234.

Example P9

Preparation of 1,3,5-trichloro-2-chloromethyl-benzene

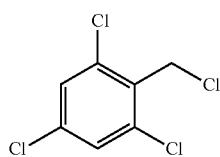 [SMILES: ClCc1c(Cl)cc(Cl)cc1Cl]

To a stirred solution of 2,4,6-trichlorobenzylalcohol (10.0 g; 47.3 mmol) in chloroform (100 ml) kept under nitrogen atmosphere, thionyl chloride (6.07 ml; 85.1 mmol) was added slowly at 0° C. over a period of 15 minutes followed by catalytic amount of DMF. The reaction mix was allowed to stir at ambient temp for 3 hours. The reaction mixture was quenched with 50 ml of water; the aqueous layer was extracted with DCM (3×100 ml). The combined organic layer was washed with 5% sodium bicarbonate solution (2×50 ml) followed by brine (50 ml) and dried over anhydrous sodium sulphate. The solvent was evaporated under reduced pressure. 10.9 g (100% of theory) of 1,3,5-trichloro-2-chloromethyl-benzene was obtained in form of a white solid.

$^1$H NMR (400 MHz, CHLOROFORM-d) δ ppm 7.37 (s, 2 H); 4.82 (s, 2 H)

MS [M+H]$^+$231/233.

Example P10

Preparation of 1-(2,4-dichloro-phenyl)-3-hydroxy-propan-2-one O-methyl-oxime a) Preparation of 3-(2,4-dichloro-phenyl)-2-(hydroxyimino)-propionic acid methyl ester

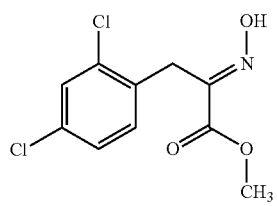 [SMILES: COC(=O)/C(Cc1ccc(Cl)cc1Cl)=N/O]

To a stirred solution of 2-(2,4-dichloro-benzyl)-malonic acid diethyl ester (6.4 g; 20 mmol) in methanol (30 ml) under argon at 23° C., was added dropwise a solution of sodium methoxide 5.4 M in methanol (4.3 ml; 23 mmol), resulting in a small exothermic (25° C.) reaction. After addition the reaction mixture was cooled to 10° C. Isoamyl nitrite (3.2 ml; 22 mmol) was added dropwise to the cooled mixture (temperature kept below 15° C.). The mixture was stirred for 2 hours at 10° C. and 1 h at 23° C. 2 N hydrochloric acid (10 ml) was added to the mixture which was stirred at 23° C. for 30 min. The reaction mixture was then poured in brine (200 ml) and extracted with ethyl acetate (3×100 ml). Combined organics were dried over sodium sulfate and evaporated under reduced pressure to give the crude solid which was recrystallized at 5° C. from cyclohexane to afford 2.5 g (48% of theory) of 3-(2,4-dichloro-phenyl)-2-(hydroxyimino)-propionic acid methyl ester as a white powder (melting point: 97-100° C.).

$^1$H NMR (400 MHz, CHLOROFORM-d) δ ppm 3.84 (s, 3 H), 4.06 (s, 2 H), 7.08 (d, J=8.1 Hz, 1 H), 7.16 (dd, J=8.4, 1.8 Hz, 1 H), 7.39 (d, J=2.2 Hz, 1 H), 9.21 (br. s., 1 H)

MS [M+H]$^+$262/264.

b) Preparation of 3-(2,4-dichloro-phenyl)-2-(methoxyimino)-propionic acid methyl ester

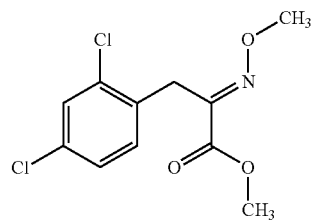 [SMILES: CO/N=C(\Cc1ccc(Cl)cc1Cl)C(=O)OC]

To a stirred suspension of 3-(2,4-dichloro-phenyl)-2-(hydroxyimino)-propionic acid methyl ester (2.0 g; 7.6 mmol) and potassium carbonate (3.2 g; 23 mmol) in N,N-dimethylformamide (15 ml) under argon at 20° C., was added drop wise methyl iodide (4.3 ml; 23 mmol). The mixture was stirred for 2 hours at 20° C. Water (300 ml) was added to the mixture which was extracted with ethyl acetate (3×150 ml). Combined organics were concentrated, the residue dissolved in 20 ml of dichloromethane, washed twice with water (150 ml), dried over sodium sulfate and evaporated under reduced pressure to afford 2.0 g (95% of theory) of 3-(2,4-dichlorophenyl)-2-(methoxyimino)-propionic acid methyl ester (mixture of E/Z-isomers) as a clear yellow oil.

Isomer 1 (70%):
$^1$H NMR (400 MHz, CHLOROFORM-d) δ ppm 3.85 (s, 3 H), 3.99 (s, 2 H), 4.07 (s, 3 H), 7.01 (d, J=8.4 Hz, 1 H), 7.13 (d, J=1.8 Hz, 1 H), 7.37 (d, J=2.2 Hz, 1 H)

Isomer 2 (30%):
$^1$H NMR (400 MHz, CHLOROFORM-d) δ ppm 3.81 (s, 3 H), 4.11 (s, 2 H), 4.22 (s, 3 H), 7.10 (d, J=8.4 Hz, 1 H), 7.15 (d, J=2.2 Hz, 1 H), 7.36 (d, J=2.2 Hz, 1 H)

MS [M+H]$^+$276/278.

c) Preparation of 1-(2,4-dichloro-phenyl)-3-hydroxy-propan-2-one O-methyl-oxime

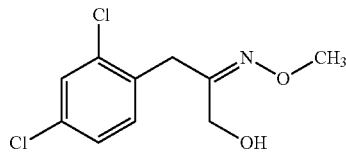

To a stirred solution of 3-(2,4-dichloro-phenyl)-2-(methoxyimino)-propionic acid methyl ester (isomers E/Z) (0.25 g; 0.90 mmol) in diethyl ether (4.0 ml) under argon at 0° C., was added portionwise sodium borohydride (0.14 g; 3.6 mmol). The mixture was stirred for 2 hours at 0° C. and allowed to warm up at 20° C. for 16 h. The mixture was poured carefully in 2 N hydrochloric acid (6 ml) and extracted with ethyl acetate (3×5 ml). Combined organics were dried over sodium sulfate and evaporated under reduced pressure. The crude oil obtained was subject to flash chromatography (eluant: c-hexane/ethyl acetate 7:3) to afford 65 mg (30% of theory) of 1-(2,4-dichloro-phenyl)-3-hydroxy-propan-2-one O-methyl-oxime (mixture of E/Z-isomers) as a clear sticky oil.

Isomer 1 (50%):
$^1$H NMR (400 MHz, CHLOROFORM-d) δ ppm 2.56 (br. s, 1 H), 3.77 (s, 2 H), 3.92 (s, 3 H), 4.09 (s, 2 H), 7.17 (s, 1 H), 7.18 (d, J=1.8 Hz, 1 H), 7.38 (d, J=1.8 Hz, 1 H)

Isomer 2 (50%):
$^1$H NMR (400 MHz, CHLOROFORM-d) δ ppm 2.40 (br. s., 1 H), 3.70 (s, 2 H), 3.88 (s, 3 H), 4.29 (br. s., 2 H), 7.21 (d, J=1.8 Hz, 1 H), 7.22 (s, 1 H), 7.39 (d, J=1.8 Hz, 1 H)

MS [M+H]$^+$248/250.

Tables 1 to 6: Compounds of Formula Ia:

The invention was further illustrated by the preferred individual compounds of formula (Ia) listed below in Tables 1 to 6. Characterising data are given in Table 9.

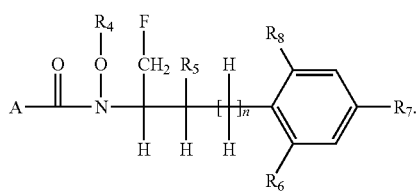
(Ia)

In the compounds of formula Ia, A is selected from the groups consisting of $A_1$,

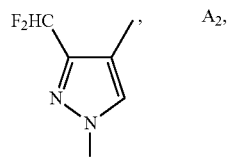
($A_1$)

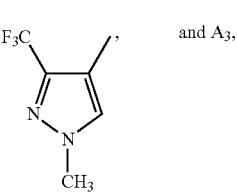
($A_2$)

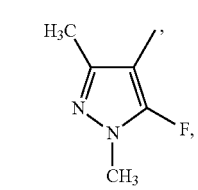
($A_3$)

and n is 0 or 1.

Each of Tables 1 to 6, which follow the Table Y below, comprises 30 compounds of the formula (Ia) in which $R_4$, $R_5$, $R_6$, $R_7$ and $R_8$ have the values given in Table Y and A has the value given in the relevant Table 1 to 6 and n has the value given in the relevant Table 1 to 6. Thus Table 1 corresponds to Table Y when Y is 1 and A has the value given under the Table 1 heading, Table 2 corresponds to Table Y when Y is 2 and A has the value given under the Table 2 heading, and so on for Tables 3 to 6.

In Tables 1 to 6 below "Me" signifies methyl, "Et" signifies ethyl and "t-Bu" signifies tertiary butyl.

TABLE Y

| Cpd No. | $R_4$ | $R_5$ | $R_6$ | $R_7$ | $R_8$ |
|---|---|---|---|---|---|
| Y.001 | Me | H | Cl | H | H |
| Y.002 | Me | H | H | Cl | H |
| Y.003 | Me | H | Cl | Cl | H |
| Y.004 | Me | H | Cl | Cl | Cl |
| Y.005 | Me | H | Cl | Br | Cl |
| Y.006 | Me | H | Cl | I | Cl |
| Y.007 | Me | H | Cl | Me | Cl |
| Y.008 | Me | H | Cl | CF$_3$ | Cl |
| Y.009 | Me | H | Cl | C≡CH | Cl |
| Y.010 | Me | H | Cl | t-Bu | Cl |
| Y.011 | Me | H | H | 4-Cl-phenyl | H |
| Y.012 | Me | H | Cl | 4-Cl-phenyl | H |
| Y.013 | Me | H | Cl | 4-Cl-phenyl | Cl |
| Y.014 | Me | H | H | 4-Cl-phenoxy | H |
| Y.015 | Me | H | Cl | 4-Cl-phenoxy | H |
| Y.016 | Me | H | Cl | 4-Cl-phenoxy | Cl |
| Y.017 | Me | H | Me | Cl | H |
| Y.018 | Me | H | Me | Cl | Cl |
| Y.019 | Me | H | Me | Me | Cl |
| Y.020 | Me | H | Me | Me | Me |
| Y.021 | Me | H | Me | t-Bu | Me |
| Y.022 | Me | H | Br | Br | H |
| Y.023 | Me | H | Br | Br | Br |
| Y.024 | H | H | Cl | Cl | Cl |
| Y.025 | H | Me | Cl | Cl | Cl |
| Y.026 | H | H | Cl | Br | Cl |
| Y.027 | H | Me | Cl | Br | Cl |
| Y.028 | Et | H | Cl | Cl | Cl |
| Y.029 | Me | Me | Cl | Cl | H |
| Y.030 | Me | Me | Cl | Cl | Cl |

Table 1 provides 30 compounds of formula (Ia), wherein A is $A_1$

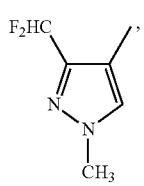
(A_1)

n is 0, and $R_4$, $R_5$, $R_6$, $R_7$ and $R_8$ are as defined in Table Y.

For example, compound 1.001 has the following structure:

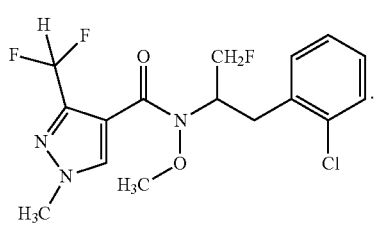
(1.001)

Table 2 provides 30 compounds of formula (Ia), wherein A is $A_1$

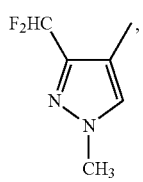
(A_2)

n is 1, and $R_4$, $R_5$, $R_6$, $R_7$ and $R_8$ are as defined in Table Y.

For example, compound 2.002 has the following structure:

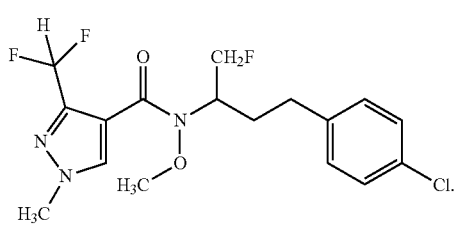
(2.002)

Table 3 provides 30 compounds of formula (Ia), wherein A is $A_2$

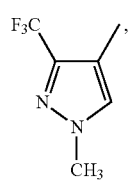
(A_2)

n is 0, and $R_4$, $R_5$, $R_6$, $R_7$ and $R_8$ are as defined in Table Y.

For example, compound 3.003 has the following structure:

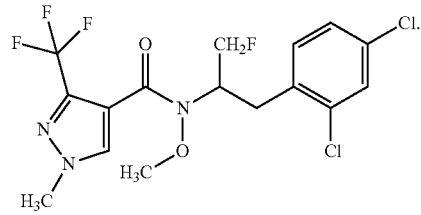
(3.003)

Table 4 provides 30 compounds of formula (Ia), wherein A is $A_2$

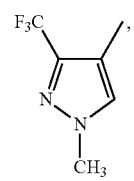
(A_2)

n is 1, and $R_4$, $R_5$, $R_6$, $R_7$ and $R_8$ are as defined in Table Y. For example, compound 4.004 has the following structure:

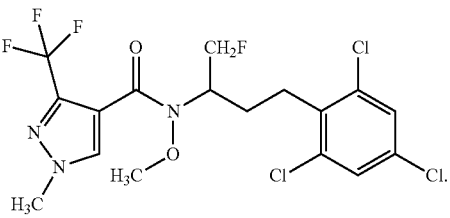
(4.004)

Table 5 provides 30 compounds of formula (Ia), wherein A is $A_3$

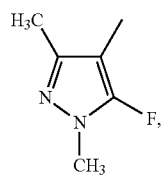
(A_3)

n is 0, and $R_4$, $R_5$, $R_6$, $R_7$ and $R_8$ are as defined in Table Y. For example, compound 5.004 has the following structure:

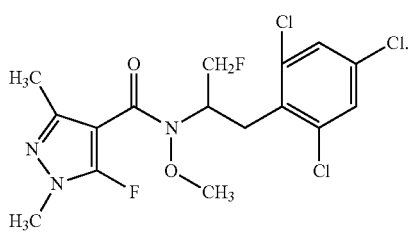
(5.004)

Table 6 provides 30 compounds of formula (Ia), wherein A is $A_3$

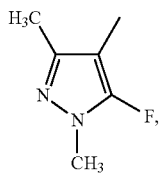

(A₃)

n is 1, and $R_4$, $R_5$, $R_6$, $R_7$ and $R_8$ are as defined in Table Y. For example, compound 6.005 has the following structure:

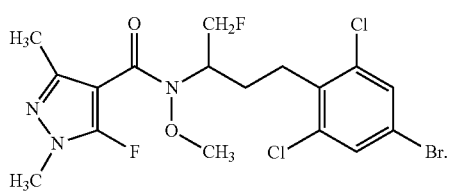

(6.005)

Tables 7 and 8:

Each of Tables 7 to 8, which follow the Table Y above, comprises 30 compounds of the formula (IIb) in which $R_4$, $R_5$, $R_6$, $R_7$ and $R_8$ have the values given in Table Y and n has the value given in the relevant Table 7 to 8. Thus Table 7 corresponds to Table Y when Y is 7, Table 8 corresponds to Table Y when Y is 8.

Table 7 provides 30 compounds of formula (IIb)

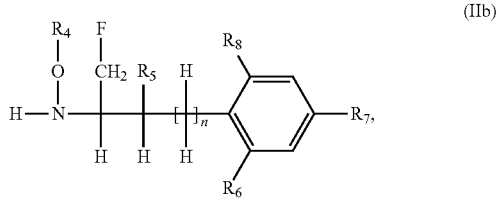

(IIb)

wherein n is 0, and $R_4$, $R_5$, $R_6$, $R_7$ and $R_8$ are as defined in Table Y.

For example, compound 7.020 has the following structure:

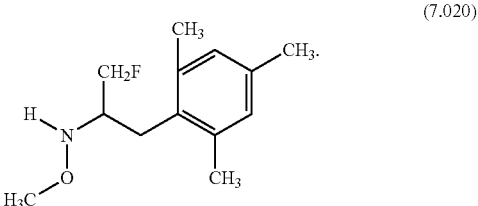

(7.020)

Table 8 provides 30 compounds of formula (IIb) wherein n is 1, and $R_4$, $R_5$, $R_6$, $R_7$ and $R_8$ are as defined in Table Y.

For example, compound 8.002 has the following structure:

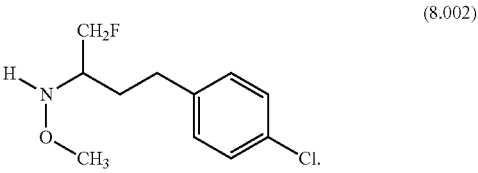

(8.002)

Table 9: Characterising Data:

Table 9 shows selected melting point and selected NMR data for compounds of Table 1 to 6. $CDCl_3$ is used as the solvent for NMR measurements, unless otherwise stated. If a mixture of solvents is present, this is indicated as, for example: $CDCl_3/d_6$-DMSO). No attempt is made to list all characterising data in all cases.

In Table 9 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

m.p.=melting point b.p.=boiling point.
S=singlet br=broad
d=doublet dd=doublet of doublets
t=triplet q=quartet
m=multiplet ppm=parts per million

TABLE 9

| Cpd No. | 1H-NMR data: ppm (multiplicity/number of Hs) | MS [M + H]⁺ | m.p. (° C.) | LCMS data |
|---|---|---|---|---|
| 1.003 | 3.02-3.31 (m, 2 H), 3.59 (s, 3 H), 3.96 (s, 3 H), 4.50-4.90 (m, 2 H), 4.75-4.87 (m, 1 H), 7.13 (t, J = 55.0 Hz, 1 H), 7.14 (dd, J = 8.4, 2.2 Hz, 1 H), 7.21 (d, J = 8.1 Hz, 1 H), 7.37 (d, J = 1.8 Hz, 1 H), 7.73 (br. s., 1 H). | 410/412 | oil | |
| 1.004 | 3.20-3.53 (m, 4 H), 3.68 (s, 3 H), 3.99 (s, 3 H), 4.43-5.00 (m, 4 H), 4.77-4.89 (m, 1 H), 7.17 (t, J = 53.0 Hz, 1 H), 7.32 (s, 2 H), 7.85 (s, 1 H). | 444/446/448 | 117-118 | |
| 2.002 | 1.78-1.94 (m, 1 H), 2.11-2.28 (m, 1 H), 2.55-2.78 (m, 2 H), 3.73 (s, 3 H), 3.99 (s, 3 H), 4.38-4.80 (m, 3 H), 7.10 (d, J = 8.1 Hz, 2 H), 7.23 (t, J = 52.0 Hz, 1 H), 7.23 (d, J = 8.4 Hz, 2 H), 7.84 (br. s., 1 H). | 390/392 | oil | |
| 3.004 | 3.22-3.51 (m, 2 H), 3.63 (br. s., 3 H), 3.98 (s, 3 H), 4.39-4.98 (m, 2 H), 4.72-4.85 (m, 1 H), 7.33 (s, 2 H), 7.75 (br. s., 1 H). | 462/464/466 | 131-133 | |

TABLE 9-continued

| Cpd No. | 1H-NMR data: ppm (multiplicity/number of Hs) | MS [M + H]+ | m.p. (° C.) | LCMS data |
|---|---|---|---|---|
| 5.004 | 2.25 (s, 3 H), 3.13-3.46 (m, 2 H), 3.67 (s, 3 H), 3.69 (s, 3 H), 4.38-4.97 (m, 3 H), 7.32 (s, 2 H). | 426/428/430 | oil | |
| 7.003 | 2.80-3.00 (m, 2 H), 3.30-3.45 (m, 1 H), 3.54 (s, 3 H), 4.30-4.60 (m, 2 H), 5.70 (s, 1 H), 7.18-7.25 (m, 2 H), 7.40 (s, 1 H). | 252/254 | oil | |
| 7.004 | 3.02-3.22 (m, 2 H), 3.44-3.52 (m, 1 H), 3.53 (s, 3 H), 4.48 (ddd, J = 47.0, 5.1, 2.2 Hz, 2 H), 5.76 (br. s, 1 H), 7.34 (s, 2 H). | 286/288/290 | oil | |
| 8.002 | 1.63-1.86 (m, 2 H), 2.64-2.81 (m, 2 H), 2.98-3.11 (m, 1 H), 3.55 (s, 3 H), 4.33-4.58 (m, 2 H), 5.69 (br. s, 1 H), 7.13 (d, J = 8.1 Hz, 2 H), 7.26 (d, J = 8.1 Hz, 2 H) | 232/234 | oil | |

Formulation Examples for Compounds of Formula I

Example F-1.1 to F-1.2

Emulsifiable Concentrates

| Components | F-1.1 | F-1.2 |
|---|---|---|
| compound of Tables 1-6 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Tables 1-6 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1-6 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1-6 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1-6 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1-6 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1-6 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Examples

Fungicidal Action

Example B-1

Action Against *Botrytis cinerea*—Fungal Growth Assay

Conidia of the fungus from cryogenic storage was directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 3-4 days. The activity of a compound was expressed as fungal growth inhibition (0=no growth inhibition, ratings of 80% to 99% mean good to very good inhibition, 100%=complete inhibition). Compounds 1.003 and 1.004 show very good activity in this test (≥80% inhibition).

Example B-2

Action Against *Mycosphaerella arachidis* (Early Leaf Spot of Groundnut; *Cercospora arachidicola* [Anamorph])—Fungal Growth Assay Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 6-7 days. The activity of a compound was expressed as fungal growth inhibition (0=no growth inhibition, ratings of 80% to 99% mean good to very good inhibition, 100%=complete inhibition). Compounds 1.003 and 1.004 show very good activity in this test (≥80% inhibition).

Example B-3

Action Against *Septoria tritici*—Fungal Growth Assay

Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was determined photometrically after 72 hrs. The activity of a compound was expressed as fungal growth inhibition (0=no growth inhibition, ratings of 80% to 99% mean good to very good inhibition, 100%=complete inhibition). Compounds 1.003 and 1.004 show very good activity in this test (≥80% inhibition).

Example B-4

Action Against *Monographella nivalis* (Anamorph: *Fusarium nivale, Microdochium nivale*; Snow Mould)—Fungal Growth Assay Conidia of the fungus from cryogenic storage were directly mixed into nutrient broth (PDB potato dextrose broth). After placing a DMSO-solution of the test compounds (0.002% active ingredient) into a microtiter plate (96-well format) the nutrient broth containing the fungal spores was added. The test plates were incubated at 24° C. and the inhibition of growth was measured photometrically after 72 hrs (0=no growth inhibition, ratings of 80% to 99% mean good to very good inhibition, 100%=complete inhibition). Compounds 1.003 and 1.004 show very good activity in this test (≥80% inhibition).

Example B-5

Action Against *Erysiphe graminis* f.sp. tritici (Wheat Powdery Mildew)

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 7 days after inoculation as preventive fungicidal activity.

Compounds 1.003 and 1.004 show very good activity in this test (≥80% inhibition).

Example B-6

Protective Action Against *Puccinia recondita* (Brown Rust) on Wheat

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 8 days after inoculation as preventive fungicidal activity.

Compounds 1.003 and 1.004 show very good activity in this test (≥80% inhibition).

Example B-7

Curative Action Against *Puccinia recondita* (Brown Rust) on Wheat

Wheat leaf segments were placed on agar in multiwell plates (24-well format) and inoculated with a spore suspension of the fungus. One day after inoculation the leaf segments were sprayed with test solutions (0.02% active ingredient). After appropriate incubation the activity of a compound was assessed 8 days after inoculation as curative fungicidal activity.

Compounds 1.003 and 1.004 show very good activity in this test (≥80% inhibition).

Example B-8

Action Against *Pyrenophora teres* (Net Blotch) on Barley

Barley leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 4 days after inoculation as preventive fungicidal activity. Compounds 1.003 and 1.004 show very good activity in this test (≥80% inhibition).

What is claimed is:

1. A compound of formula I (I)

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$halogenalkyl;
$R_5$ is hydrogen, halogen, $C_1$-$C_4$alkyl or $C_1$-$C_4$halogenalkyl;
$R_6$ is hydrogen, halogen, $C_1$-$C_4$alkyl, $C_2$-$C_6$alkenyl or $C_3$-$C_6$alkinyl;
$R_7$ is hydrogen, halogen, $C_1$-$C_6$alkyl, $C_2$-$C_6$alkenyl, $C_3$-$C_6$alkinyl, $C_3$-$C_6$cycloalkyl-$C_3$-$C_6$alkinyl, halophenoxy, halophenyl-$C_3$-$C_6$alkinyl, $C_1$-$C_6$haloalkyl, $C_1$-$C_6$haloalkoxy, $C_2$-$C_6$haloalkenyl, or $C_2$-$C_6$haloalkenyloxy;
$R_8$ is hydrogen, halogen, $C_1$-$C_4$alkyl, $C_2$-$C_6$alkenyl or $C_3$-$C_6$alkinyl; with the proviso that at least one of $R_6$, $R_7$ and $R_8$ is different from hydrogen;
n is 0 or 1 or agronomically acceptable salts/stereoisomers/diastereoisomers/enantiomers/tautomers and N-oxides of those compounds.

2. A compound of formula I according to claim 1, wherein
$R_1$ is difluoromethyl, trifluoromethyl or methyl,
$R_2$ is methyl;
$R_3$ is hydrogen or fluoro;
$R_4$ is methyl;
$R_5$ is hydrogen or methyl;
n is 0; and
$R_6$, $R_7$ and $R_8$ independently from each other, are hydrogen or chloro.

3. A compound of formula I according to claim 2, wherein $R_5$ is hydrogen.

4. A compound of formula I according to claim 1, wherein
$R_1$ is difluoromethyl or trifluoromethyl;
$R_2$ is methyl;
$R_3$ is hydrogen;
$R_4$ is methyl;
$R_6$, $R_7$ and $R_8$ are, independently from each other, hydrogen or halogen.

5. A compound of formula I according to claim 4, wherein $R_6$, $R_7$ and $R_8$ are, independently from each other, hydrogen or chloro, with the proviso that at least one of $R_6$, $R_7$ and $R_8$ is different from hydrogen.

6. A compound of formula I according to claim 1, wherein $R_5$ is hydrogen.

7. A compound of formula I according to claim 1, wherein
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$ is hydrogen;
n is 0 or 1;
$R_6$ is hydrogen or halogen;
$R_7$ is halogen; and $R_8$ is hydrogen or halogen.

8. A compound of formula I according to claim 7, wherein n is 0.

9. A compound of formula II (II)

wherein
$R_4$ is hydrogen, $C_1$-$C_4$ alkyl or $C_1$-$C_4$ halogenalkyl;
$R_5$ is hydrogen, halogen, $C_1$-$C_4$ alkyl or $C_1$-$C_4$ halogenalkyl;

$R_6$ is hydrogen, halogen, $C_1$-$C_4$ alkyl, $C_2$-$C_6$ alkenyl or $C_3$-$C_6$ alkinyl;

$R_7$ is hydrogen, halogen, $C_1$-$C_6$ alkyl, $C_2$-$C_6$ alkenyl, $C_3$-$C_6$ alkinyl, $C_3$-$C_6$ cycloalkyl-$C_3$-$C_6$alkinyl, halophenoxy, halophenyl-$C_3$-$C_6$alkinyl, $C_1$-$C_6$haloalkyl, $C_1$-$C_6$haloalkoxy, $C_2$-$C_6$haloalkenyl, or $C_2$-$C_6$haloalkenyloxy;

$R_8$ is hydrogen, halogen, $C_1$-$C_6$ alkyl, $C_2$-$C_6$ alkenyl, $C_3$-$C_6$ alkinyl;

n is 0 or 1; and with the proviso that at least one of $R_6$, $R_7$ and $R_8$ is different from hydrogen.

10. A method of controlling infestation of useful plants by phytopathogenic microorganisms, wherein a compound of formula I according to claim 1 or a composition, comprising this compound as active ingredient, is applied to the plants, to parts thereof or the locus thereof.

11. A composition for controlling phytopathogenic microorganisms, comprising a compound of formula I according to claim 1 and an inert carrier.

* * * * *